Patent Number: 4,882,425
Date of Patent: Nov. 21, 1989

[54] RECEPTOR SPECIFIC PROTEINS AND THEIR USE IN RECEPTOR TYPING

[75] Inventors: Richard A. Hull; Sheila I. Hull; Bogdan Nowicki, all of Houston, Tex.

[73] Assignee: Baylor College of Medicine, Houston, Tex.

[21] Appl. No.: 72,197

[22] Filed: Jul. 9, 1987

[51] Int. Cl.$^4$ .......................... C07K 15/04; C07K 15/14
[52] U.S. Cl. ..................................... 530/396; 530/395; 530/350; 530/820; 530/825; 435/68; 435/70; 436/827
[58] Field of Search ............... 530/350, 396, 395, 825; 435/68; 436/827

[56] References Cited

U.S. PATENT DOCUMENTS

| | | | |
|---|---|---|---|
| 4,247,452 | 1/1981 | Irons et al. ........................... | 530/396 |
| 4,298,689 | 11/1981 | Doyle et al. . | |
| 4,457,865 | 7/1984 | Miller ................................... | 530/396 |
| 4,520,111 | 5/1985 | Miller ................................... | 530/396 |

OTHER PUBLICATIONS

Karhi et al., Bichem. Biophys. Acta, 622, 344–54, (1980).
Rhen et al., J. Bacteriol., 168:1234–42, (1986).
Lis et al., Ann. Rev. Bioch., 55, 35–67, (1986).
J. Immunol., Boyd, W. C. and Reguera, R. M., 62:333–339, (1949).
J. Path. Bact., Duguid, J. P. et al., 70:335–348, (1955).
Receptors Specific Proteins, Gold. E. R. and Balding, P., American Elsevier Publishing Company, New York, pp. 6–8, 77–115, 165–173, 391–403, (1975).
Zentialblatt Fur Bakteriologie, Parasitenkunde, Infehtionskrankheiten und Hygiene, Guyot, G., 47:640–653, (1908).
*Infection & Immunity*, Korhonen, T. K. et al., 27:569–575, (1980).
Infection & Immunity, Korhonen, T. K. et al., 54:382–332, (1986).
*FEMS Microbiology Letters*, Korhonen, T. K. et al., 35:313–318, (1986).
J. Ann. Rev. Biochem., Lis, H. and Sharon, N., 55:35–67, (1986).
*Microbiological Microbial Lectins and Agglutinins*, Mirelman, D. and Ofek, I., John Wiley and Sons, New York, pp. 1–19, (1986).
*Microbial Pathogenesis*, Nowicki, B. et al., 1:169–180, (1986).
Adhesins and Colonization Factors of *Escherichia coli*, Perry, S. H. and Rooke, D. M. in M. Sussman, ed., *The Virulence of Escherichia coli*, Academic Press, London, pp. 79–155, (1985).
Blood Groups in Man, Race, R. R. and Sanger, R., Blackwell Scientific Publications, Oxford, pp. 54–59, 122–124, 395–401, 464–465, 486–491, (1975).
Ann. Med. Exp., Fenn. Renkonen, K. O., 26:66–72, (1948).
Journal of Bacteriology, Rhen, M. et al., 168:1234–1242, (1986).
Human Blood Groups, Salmon, C. et al., Masson Publishing, New York, pp. 49, 159, 240–248, 469, (1984).
*Sigma Catalog*, (1987), list of Lectins, pp. 808–811.
Technical Manual, American Association of Blood Banks, Arlington, Va., (1985), pp. 427–428.
Lectins, Wadstrom, T. et al., Degruyter Company Berlin, pp. 417–424, (1985).
*Laboratory Medicine Hematology*, Sixth Edition, Miale, J. B., C. V. Mosby, Co., St. Louis, pp. 495–496, (1982).
FEMS Microbiol. Lett., van Alphen, L. et al., 37:69–71, (1986).
Vox Sang, Bird, G. W. G. and Wingham, J., 24:48–56, (1973).

*Primary Examiner*—Margaret Moskowitz
*Assistant Examiner*—Jeff Kushan
*Attorney, Agent, or Firm*—Fulbright & Jaworski

[57] ABSTRACT

Described is composition of matter and methods useful for the indentification of blood group antigens. Additionally a kit which can be used to identify and quantify a large number of blood group antigens is disclosed. The composition of matter and the methods can be used to identify antigens on red blood cells, as well as, on tissue samples.

4 Claims, No Drawings

RECEPTOR SPECIFIC PROTEINS AND THEIR USE IN RECEPTOR TYPING

FIELD OF THE INVENTION

The present invention relates generally to receptor specific proteins and their use in blood and tissue typing and disease detection and monitoring.

BACKGROUND OF THE INVENTION

Proteins that bind to specific sites on the surface of human animal erythrocytes and/or to sites on other tissues have been variously called agglutinins, lectins, antibody like substances or receptor specific proteins (RSPs). We prefer the more general term RSP which has been defined to mean proteins or glycoproteins that recognize and bind to specific receptors but which have no known biological function as do hormones, drugs and neurotransmitters. Gold and Balding *Receptor Specific Proteins,* American Elsevier Publishing New York (1975). The value of RSPs for such uses as blood group determination, bacterial typing, histological and cytochemical staining, cell separation and mitogenic stimulation of lymphocytes has become readily apparent. Lis and Sharon Ann. Rev. Biochem. 55: 35-67 (1986).

The first blood group specific RSPs were obtained from extracts of certain plants. Race and Sanger, *Blood Groups in Man* Blackwell Scientific Publications 6th ed Oxford pp. (1975). These RSPs were specific for the $A_1$ antigen of the ABO blood group system and could be used to distinguish $A_1$ from $A_2$ cells. Presently, a variety of RSPs found in extracts of plant or animal tissues are known to have blood group specificity. Race and Sanger; Gold and Balding (1975). Examples include RSPs with specificity for the $A_1$, A, D, M, N, T, Sd and Cad serological groups. Although RSP blood typing is limited by the small number of blood groups recognized, RSPs have an advantage over antibody preparations because they are more specific and do not cross-react with closely related antigens.

Adherence of bacteria to animal erythrocytes was first reported in 1908. Guyout, Zentialblatt fur Bakteriologie, Parasitenkunde, Infektionskrankhecten und Hygiene 47: 640-653 (1908). Subsequently, it was demonstrated that organized fibrous appendages, on the surface of bacteria, called fimbriae or pili, mediated hemagglutination. Duguid J. Path. Bact. 70: 335-348 (1955). The adherence organelles have an important role as colonization factors in the early stages of bacterial infection. Initially, the binding specificity of these RSPs was defined by the amount of D-mannose inhibition of adherence. The bacteria were classified as mannose sensitive (MS) or mannose resistant (MR). The MS RSPs are presumed to recognize a mannose containing receptor, are called "Type 1" fimbriae, and have been identified on many members of the family Enterobacteriaceae. On the other hand, MR RSPs are divided into groups based on their antigenic cross reactivity, subunit size and binding specificity for tissues and erythrocytes of various animal species. MR RSPs include K88, K99, 987P, F41, CFA/I, CFA/II, P, M, S and G. Of this group, only the P and M RSPs recognize specific blood group antigens. Bacteria that express P RSP will agglutinate P erythrocytes but not p̄ erythrocytes while bacteria that express M RSP will agglutinate MM and MN but not NN erythrocytes. Although plant RSPs specific for MM and MN cells are easily obtained from several species in the genus Iberis, other RSPs specific to blood group antigens have been rarely discovered.

SUMMARY OF THE INVENTION

An object of the present invention is the isolation, identification and cloning of receptor specific proteins.

An additional object of the present invention is the use of receptor specific proteins for blood and tissue typing.

Another object of the present invention is the development of an easy, cost efficient method of typing blood and staining tissues.

A further object of the present invention is a method of isolating fimbriae from bacteria.

Another object of the present invention is a kit for typing blood and for staining tissues.

An additional object of the present invention is the use of receptor specific proteins for detection of disease.

A further object of the present invention is a recombinant DNA bacterium coding for receptor specific protein.

An additional object of the present invention is the isolation, identification and cloning of receptor specific proteins with specificity to the blood and tissue antigens En(a+), En(a−), Dr+, Dr−, Dr−$Cm^R$. KK, kk, Kk, $K_o$, Pglobo and Anton.

Thus, in accomplishing the foregoing objects there is provided in accordance with one aspect of the present invention the provision as a composition of matter, a receptor specific protein having an antigen specificity to an erythrocyte antigen. The specificity is to an antigen selected from the group consisting of En(a+), En(a−), Dr+, Dr−, Dr−$CM^R$, KK, Kk, kk, $K_o$, Pglobo and Anton.

A futher aspect of the present invention is a composition of matter, a receptor specific protein having an antigen specificity to a tissue antigen selected from the group consisting of En(a+), En(a−), Dr+, Dr−, Dr−$CM^R$, KK, Kk, kk, $K_o$, Pglobo and Anton.

Another aspect of the present invention is a composition of matter, a recombinant DNA *E. coli* having a gene coding for a receptor specific protein. The receptor specific protein has a specificity for antigens selected from the group consisting of En(a+), En(a−), Dr+, Dr−, Dr−$CM^R$, KK, Kk, kk, $K_o$, Pglobo and Anton. Advantageously the selected receptor specific protein is selected from the group consisting of Dr+ and Dr−.

There is provided in accordance with another aspect of the present invention a kit for detecting antigens, comprising, at least one receptor specific protein having a specificity to antigens selected from the group consisting of En(a+), En(a−), Dr+, Dr−, Dr−$CM^R$, KK, Kk, kk, $K_o$, Pglobo and Anton. One embodiment of the kit includes in addition to at least one receptor specific protein, at least one control antigen selected from the group consisting of En(a+), En(a−), Dr+, Dr−, Dr−$CM^R$, KK, Kk, kk, $K_o$, Pglobo and Anton.

A further aspect of the present invention is the development of a method of purification of receptor specific protein, comprising the steps of growing bacteria in a fimbriae enhancing environment, removing the fimbriae from the bacteria, and preserving the fimbriae. Advantageously the preserving of the fimbriae includes the adding of a preserving agent selected from the group consisting of metabolic poisons, chelaters, heat fixation, radiation, paraformaldehyde, formaldehyde and gluteraldehyde. In one specific embodiment approximately 1.8% paraformaldeye is used as the preserving agent. After the fimbriae have been preserved they can be stored for future use.

An additional aspect of the present invention is the method of staining tissue comprising the step of reacting the tissue with at least one receptor specific protein. The receptor specific protein has a tissue antigen selected from the group consisting of En(a+), En(a−), Dr+, Dr−, Dr−CM$^R$, KK, Kk, kk, K$_o$, Pglobo and Anton.

Another aspect of the present invention is a method of detecting disease which includes the use of at least one receptor specific protein. Furthermore, one aspect includes a method of blood typing using at least one receptor specific protein. In both the detection of disease and in the blood typing kits can be used.

Further objects, features and advantages will be apparent from the following description of preferred embodiment of the invention.

DESCRIPTION

Receptor specific proteins (RSP), also known as lectins, from bacterial sources have been isolated and identified for specificity to antigens on the surface of cells. One embodiment is a composition of matter, a RSP having an antigenic specificity to an erythrocyte antigen selected from the group consisting of En(a+), En(a−), Dr+, Dr−, DR−CM$^R$, KK, Kk, kk, K$_o$, Pglobo and Anton. The RSPs are used to detect antigens on the surface of erythrocytes (red blood cells) to identify specific blood groups. An additional embodiment employs, as a composition of matter a RSP having an antigen specificity to a tissue antigen selected from the group consisting of En(a+), En(a−), Dr+, Dr−, Dr−CM$^R$, KK, Kk, kk, K$_o$, Pglobo and Anton. This RSP is used to detect antigens on the surface of other cells, for example kidney, gut and skin.

P specific RSPs can be used to define the organization of the P antigen in normal human kidneys. P RSP binds to the lumen of tubules, to the cytoplasm and lumen of collecting ducts and to the parietal epithelium in the glomerulus. Dr specific RSP is distributed in a variety of human tissues including gut, kidney, skin, breast and uterus. In the kidney the antigen is localized in the interstitial tissue on basement membranes.

RSPs have been found in a variety of organisms including plants and bacteria. The isolated RSPs and recombinant DNA RSPs of the present invention are obtained from bacteria. The RSPs are filamentous appendages and accessory proteins found on the bacterial surface, and are known as fimbriae or pili. The bacteria use these fibers to adhere (bind) to the surface of cells. This adhesive capacity is an important stage in causing infection. The binding of fimbriae to the surface of erythrocytes leads to hemagglutination. Because of their binding specificity, these fimbriae provide an ideal detection system for the identification and measurement of antigens on the surface of erythrocytes and thus are useful in blood typing. Additionally, the ability of the RSPs to bind to any cell surface which contains the specific antigen is useful in the detection of disease states.

The present invention describes newly identified RSPs which bind to a variety of antigens on the surface of erythrocytes and tissues. This binding is achieved by the attachment of the fimbriae to the receptors on the cell surface. Although RSPs usually bind the carbohydrate moiety of the antigen other biochemical groups are also recognized by the fimbriae. In the present invention the fimbriae are mixed with either erythrocytes or tissue and the binding is measured quantitatively. The erythrocytes which bind the fimbriae will hemagglutinate. Thus, the presence or absence of the antigen is detected by observing the cells shortly after the addition of the fimbriae.

One specific embodiment as a composition of matter is a RSP having a hemagglutination specificity to an erythrocyte antigen En(a+). This new system has been isolated, purified and identified and the RSP binds to the surface antigen receptor in the En(a) blood group system. In this instance, a fimbriae isolated from bacteria binds to the En(a+) antigen resulting in agglutination. This RSP is ideally suited for the specific detection of En(a+) and En(a−) blood groups. As shown in table 1 a variety of samples were tested using whole bacteria fimbriae. The RSP bound and agglutinated En(a+) cells but did not bind or agglutinate En(a−) cells.

TABLE 1

| Agglutination of erythrocytes by *Escherichia coli* HU1005. | | | |
|---|---|---|---|
| Red Cell Blood Type | Hemagglutination | Red Cell Blood Type | Hemagglutination |
| O bombay | + | Emm− | + |
| Bk | + | Yt (a−) | + |
| Luke− | + | Co (a−b−) | + |
| Rh null | + | Tc (a−b−c−) | + |
|  |  | Cr (a−) |  |
| Lu (a−b−) Dominant | + | I− | + |
| Lu (a−b−) Recessive | + | Hy−Gy− | + |
| Ko | + | JMH− | + |
| U− | + | Rg− | + |
| Ge −1−2−3 | + | Ch− | + |
| Jk (a−b−) | + | Yk (a−) | + |
|  |  | Cs (a−) |  |
| Lan− | + | Ku (a−) | + |
|  |  | McC (a−) |  |
| Sc −1−2 | + | Tc (a−) | + |
| En (a−) | − | Cr (a−) | + |
| Wr (b−) | + | Gill− | + |
| Ge−Leach type | + | In (b−) | + |
| At (a−) | + | Au (a−) | + |
| Jr− | + | Monkey cells | − |
| Di (b−) | + | Dog cells | + |
| Er (a−) | + | Sheep cells | + |
| Ok (a−) | + |  |  |

This antigen was further characterized to determine the binding site and the receptor specificity. Bacteria or fimbriae with En(a+) specificity did not hemagglutinate erythrocytes which have been treated with papain, ficin or *Staphylococcus aureus* V8 protease. These enzymes cut the glycophorin A molecule at defined positions. Ficin cuts at amino acid position 49 and V8 protease cuts at amino acid position 57. The region of glycophorin A between amino acids 47 and 56 is called the FS region and contains the receptor for the RSP from *E. coli* strain HU1005. These results indicate high specificity of the RSP to the antigen for En(a+).

The binding site on the RSP was further characterized by trypsin neuraminidase digestion. This treatment enhanced the hemagglutination reaction. Trypsin neuraminidase treatment removed the N terminal 39 amino acids adjacent to the En(a)FS region in glycophorin A, the sialic acid residues from glycophorin A, as well as other sialic acid residues from erythrocyte antigens. Sialic acid is a known receptor for other bacterial RSPs. After removal of the N terminal amino acids as well as the sialic acids there was enhanced agglutination, suggesting that there was a conformational change resulting in the opening up of the receptor site, for increased binding with the RSP. The erythrocyte receptor for the En(a+) RSP includes all or part of the region of the glycophorin A molecule between the amino acids 40 and 56 and may include part of the region between amino acids 56 and 70. However, the binding site for the RSP does not include the sialic acid residues linked to the receptor molecule.

The specificity of the En(a) RSP provides a simple test for the detection of En(a+) and En(a−) phenotypes. The use of RSPs is much more economical than the method currently employed. Additionally, there is very little false testing because of the high specificity of the RSP.

Another example as a composition of matter is a RSP having a hemagglutination specificity to the erythrocyte antigen Dr+. This fimbriae like structure was isolated from Escherichia coli IH11128. This specific RSP has been identified as 075X adhesion factor and specifically binds to the cells of the human kidney. The present invention describes the identification, characterization and use of the specific antigen specificity of this RSP. Of all the blood groups tested (Table 2), the only positive agglutination between these blood groups and the isolated RSP was with the IFC blood group complex.

TABLE 2

Hemagglutination of erythrocytes by selected Escherichia coli strains. (NT = not tested)

| Blood Group | Bacterial Strains | | | |
|---|---|---|---|---|
| | IH11128 | BN406 | BN53 | HU824 |
| JK (a−b−) | + | + | + | + |
| Lan− | + | + | + | + |
| Sc (a−) | + | + | + | + |
| En (a−) | + | + | + | + |
| Wr (b−) | + | + | + | + |
| Le− | + | + | + | + |
| At (a−) | + | + | + | + |
| Jr− | + | + | + | + |
| Di (b−) | + | + | + | + |
| Er (a−) | + | + | + | + |
| Emm− | + | + | + | + |
| Yt (a−) | + | + | + | + |
| IFC− | (±) | − | − | + |
| Co (a−b−) | + | + | + | + |
| I− | + | + | + | + |
| Hy−Gy− | + | + | + | + |
| JMH | + | + | + | + |
| Rg− | + | + | + | + |
| Ch− | + | + | + | + |
| Yk (a−) Cr (a−) | + | + | + | + |
| Ku (a−) McC (a−) | + | + | + | + |
| Tc (a−) | + | + | + | + |
| Cr (a−) | + | + | + | + |
| Lill− | + | + | + | + |
| In (b−) | + | + | + | + |
| an (a−) | + | + | + | + |
| Dog | − | − | − | NT |
| Sheep | − | − | − | NT |

Agglutination was observed between the Dr+ blood group antigen and the 075X fimbriae like adhesion structure. The specificity of 075X positive E. coli was measured by its hemagglutination capacity with human erythrocytes representing different blood group systems. Six E. coli strains of different hemagglutinin types were used. Recombinant DNA strains BN406 and BN407 and clinical isolates BN53 and IH11128 exhibited positive 075X binding. HU824 exhibited P-fimbriae and HU1005 exhibited hemagglutinin with En(a) receptor specificity. The 075X positive strains reacted with all erythrocyte phenotypes except IFC− and Dr− erythrocytes. Dr+ cells lacking other components of the IFC complex such as Tc−, Cr−, Es− and "Wash−" blood group antigens reacted strongly (Table 3).

TABLE 3

Reaction of red cells from individuals lacking high frequency antigens of the IFC-complex with selected E. coli strains.

| Patient or donor | | Phenotype Hemagglutination by E. coli | | | | |
|---|---|---|---|---|---|---|
| | | BN406 075X+ | BN53 075X+ | HU824 P+ | HU1005 En (a)+ | SH175 075XCmR+ |
| M.D. | Dr (a−) | − | − | + | + | − |
| N.L. | Dr (a−) | − | − | + | + | − |
| Inab | IFC− | − | − | + | + | − |
| J.F. | IFC− | − | − | + | + | − |
| D.W.L. | Tc (a−b−c+) | + | + | + | + | + |
| C.Sm. | Cr (a−) | + | + | + | + | + |
| E.E.G. | Es (a−) | + | + | + | + | + |
| T.J. | Wash− | + | + | + | + | + |

Strains with P or En(a)-hemagglutinins reacted with all the above-mentioned erythrocytes. A positive reaction of BN406 with Dr+ erythrocytes and no reaction with the IFC− and Dr− erythrocytes indicated that the Dr blood group antigen is an erythrocyte receptor for the 075X RSP. Since the 075X RSP binds with all cell types except Dr−, this RSP is ideally suited for use as a specific test for the presence and absence of the Dr antigen in the blood cell.

The receptor moiety in the Dr blood group antigen recognized by the 075X RSP was further characterized by the inhibitory effects of several potential receptor analogues. A commercial reagent erythrocyte diluent inhibited hemagglutination caused by the 075X positive E. coli BN53 but not by the P− and other X− fimbriated strains. Further testing demonstrated that chloramphenicol was the active inhibitory component of the reagent. Chloramphenicol in a concentration of approximately 2 $\mu$M inhibited hemagglutination (Table 4).

TABLE 4

Inhibition of hemagglutionation caused by E. coli IH11128 and BN407

| Inhibitor | Minimal Inhibitory Concentration (mM) | |
|---|---|---|
| | IH11128 | BN407 |
| Chloramphenicol | 0.002 | 0.009 |
| Chloramphenicol succinate | 0.009 | 0.018 |
| Thiamphenicol | >100 | >100 |
| Chloramphenicol base | >100 | >100 |

TABLE 4-continued

Inhibition of hemagglutionation caused by E. coli IH11128 and BN407

| Inhibitor | Minimal Inhibitory Concentration (mM) | |
|---|---|---|
| | IH11128 | BN407 |
| α-p-nitrophenyl-glycerine | 60 | >100 |
| p-nitrophenyl-β-D-glucopyranoside | >100 | >100 |
| p-nitrophenyl-β-D-glucuronide | >100 | >100 |
| p-nitrophenyl-phosphorylcholine | >100 | >100 |
| p-nitophenyl-N—acetyl-β-D-glucosaminide | >100 | >100 |
| p-nitrophenyl | >100 | >100 |
| 3-(p-hydroxyphenyl)-propionic acid | 100 | 100 |
| p-hydroxyphenyl-acetic acid | 100 | 100 |
| β-phenylpyruvic acid | >100 | >100 |
| p-hydroxyphenyl | >100 | >100 |
| t-BOC—O—benzyl-L-tyrosine | 0.3 | 0.6 |
| N—acetyl-L-tyrosine | 60 | 100 |
| α-methyl-DL-p-tyrosine methylester | 100 | >100 |
| L-tyrosyl-L-tyrosyl-L-tyrosine | 100 | >100 |
| L-tyrosine | >100 | >100 |

Furthermore, upon the addition of chloramphenicol the agglutinate was disaggregated in a few seconds into a homogeneous erythrocyte-bacteria mixture. Thus, chloramphenicol effectively eluted bacterial cells from the erythrocyte receptor. The 075X binding was further characterized by examining the specific chemical groups in the chloramphenicol structured (Table 4). Chloramphenicol analogues were shown to have differential effects on the binding of erythrocytes to IH11128 and BN407. Thiamphenicol, which has an $SO_2CH_3$ substituent added at the para position in the benzene ring, and chloramphenicol base, which lacks the acetylamide group showed no inhibitory activity. The sodium succinate chloramphenicol having a substitution at the C-3 position had an inhibitory effect at 9 μM. These tested groups on the chloramphenicol molecule are important for the expression of the full inhibitory activity.

The binding structure of the RSP was further elucidated by testing compounds which contain the p-nitrophenyl group of chloramphenicol but differ in the aliphatic part (C-1 to C-3). Analogs of p-nitrophenyl in which the aliphatic chain was substituted with glucopyranoside, glucuronide, glucosaminide or phosphorylcholine were not active. However, p-nitrophenyl-glycerol inhibited hemagglutination of IH11128 at 60 mM concentration, indicating that a three carbon aliphatic structure bound to the benzene ring is required for the compound to be active.

Further analyses at the hydroxyl group on the para position on the benzene ring demonstrated that this position is also important. 3-(p-hydroxyphenyl)-propionic acid and p-hydroxyphenylacetic acid were inhibitory at 100 mM while α-phenyl pyruvic acid missing the hydroxyl group on the benzene ring was inactive.

Compounds found in human biochemical pathways with three carbon aliphatic chains and/or p-hydroxyl groups were tested for inhibition of antigen recognition. Tert-butoxycarbonyl-O-benzyl-L-tyrosine which has 3 methyl groups at the positions analogous to the chlorine molecules in chloramphenicol inhibited hemagglutination at 0.3 mM and N-acetyl tyrosine, α-methyl-L-tyrosine methylester, and tri-tyrosine showed weak inhibitory activity. Other peptides, amino acids, sugars and chemicals tested including tyrosine and N-acetyl-tyrosineamide, L-seryl-L-tyrosine, L-leucyl-L-tyrosine, L-tyrosyl-glycine, glycl-L-tyrosine, D-tyrosyl-L-valyl-glycine, L-phenylalanine, L-alanine, leucine, serine, glycine, glucose, sucrose, D-mannose, D-ribose, p-amino salicilic acid, p-anisidine, dinitrosalicilic acid, pyruvic acid, acetamide, glycerol, propanol, gentamycin and neomycin showed no inhibitory activity.

The receptor moiety in the Dr antigen in the kidney recognized by the 075X RSP was also inhibited by chloramphenicol. This included the specific attachment of E. coli BN406 and the purified 075X RSP isolated from BN406 to the basement membrane and Bowman's capsule. The receptor molecule on the Dr antigen in erythrocytes and kidney tissue appears to be similar.

A further specific embodiment, as a composition of matter, is a RSP having a hemagglutination specificity to the erythrocyte antigen $Dr-Cm^R$. This RSP was identified, isolated and characterized for its specific activity to the $DR-CM^R+$ antigen. This structure was expressed on the surface of E. coli SH175. This RSP hemagglutinated erythrocytes that contain the Dr+ antigen on their surfaces. There was no hemagglutination when the RSP was added to Dr− erythrocytes. However, the Dr+ phenotyes are not homogeneous. Some individuals who are Dr+ contain an antigenic site called $CM^R$. The present invention isolated and characterized RSPs which can distinguish $Dr-CM^R+$ from Dr+ phenotypes. The Dr+ and $Dr-CM^R+$ were distinguishable because of their response to chloramphenicol. Whereas Dr+ was inhibited by the chloramphenicol, $Dr-CM^R+$ was not inhibited by chloramphenicol. Thus the isolated RSPs can be used to characterize the different phenotypes by the affinity of the antigenic binding sites.

Another specific embodiment, as a composition of matter, is a RSP having a hemagglutination specificity to the erythrocyte antigen selected from the group consisting of KK, Kk, kk, and $K_o$. This RSP is specific to the Kell blood group system. The RSP reacted differentially to the different phenotypes of the Kell system. The highest agglutination was found in the kk phenotype. Intermediate agglutination levels were seen in Kk and a small but positive agglutination was observed in KK phenotypes. Furthermore, the $K_o$ phenotype was not agglutinated by this RSP and thus the RSP can be used as a specific detector for $K_o$. Because this RSP binds differentially, all of the genes at the Kell locus are detected. This differential binding provided an accurate and reliable method to distinguish the various phenotypes observed in the Kell system. Table 5 demonstrates the various reactions with the different phenotypes of the Kell system, as well as, the response under a variety of inhibitor conditions. Table 5. Hemagglutination of erythrocytes by Neisseria mengitidis HU1094.

| Red Cell Blood Type | Hemagglutination | Red Cell Blood Type | Hemagglutination |
|---|---|---|---|
| Di (b−) | ++ | an (a−) | ++ |
| Er (a−) | ++ | KK | + |
| Ok (a−) | ++ | Kk | ++ |
| Yt (a−) | ++ | kk | +++ |
| Co (a−b−) | ++ | $K_0$ | − |
| I− | ++ | McLeod | +− |
| Ch− | ++ | Ge 1-2-3 | +++ |
| Yk (a−) Cr (a−) | ++ | AET treated | +− |
| Ku (a−) McC (a−) | ++ | ZZAP treated | +− |
| Tc (a−) | ++ | Ficin treated | ++ |
| Cr (a−) | ++ | Untreated | ++ |

Using these inhibitor conditions the RSP has been further identified and characterized. The molecular structure of the K and k antigens is unknown but the antigens were destroyed by treatment with the protease 2-aminoethyl isothioronium bromide (AET) or the reagent ZZAP that contains papain plus dithiothreitol. Prior treatment of K cells with AET or ZZAP altered the antigenic surface of erythrocytes such that HU1094 agglutinated the erythrocytes to a lesser extent. Treatment of red cells with ficin had no effect on the K antigen and did not affect hemagglutination by HU1094.

Currently one class of bacterial RSP recognizes a portion of the P blood group antigen, specifically the Gal-α-1->4-β-Gal digalactoside portion. Bacteria that contain the P RSP will agglutinate P but not p erythrocytes and will bind to latex beads coated with Gal-α-1->4-β-Gal or globotetraosylceramide (globoside). Although P fimbriae have been the subject of considerable study in the past 10 years, this disclosure describes the first use of this RSP for blood group determination. Although many natural occurring isolates, such as *E. coli* HU734, exist that express the P RSP, these strains are usually not acceptable for use in blood group determination. In the preferred embodiment a recombinant DNA strain that expresses only the P RSP is used. For example, HU849, which is *E. coli* P678-54 that contains the recombinant plasmid pRHU845 encoding the P RSP, can be used. Other usable recombinant plasmids are pPAP5 and pPAP22 which derive from pRHU845 and express a P RSP.

The present invention also includes another specific embodiment an *E. coli* strain, HU784, that expressed a new RSP specific for a different region of the P blood group antigens or a different P like antigen. This RSP, designated Pglobo, agglutinated P but not p̄ erythrocytes; however it bound only to latex beads coated with globotetraosylceramide. It did not bind digalactoside coated beads. Additionally, bacteria that express only the Pglobo RSP agglutinated sheep erythrocytes, while bacteria that express only P RSP did not agglutinate sheep erythrocytes. The P and Pglobo RSPs can be used jointly or separately for P blood group determination.

The recombinant plasmid that encodes the Pglobo RSP has been further characterized. The plasmid pBR322 molecules carrying a variety of 10-14 kilobase restriction endonuclease BamHl fragments from the *E. coli* SHl genome were used to transform *E. coli* HB101. Colonies that expressed the Pglobo RSP were isolated from the resulting ampicillin resistant transformants, for example, the plasmid from *E. coli* JFK102, called pJFK102, contained a 12 kb BamHl fragment. The recombinant DNA of the present invention may include the entire coding sequence of RSP or may comprise deletions or insertions as long as the resultant protein coded for binds to the specific RSP receptor.

The agglutination ability of natural strain SHl that expressed both P RSPs and of *E. coli* HU849 (strain P678-54 that contained the Pgal RSP recombinant plasmid pRHU845) and *E. coli* HU1093 (strain P678-54 that contained Pglobo plasmid pJFK102) was measured and compared with strain P678-54 alone. Dilutions of bacteria were mixed with latex beads coated with either Gal-α-1->4-β-Gal digalactoside or globoside and the resultant agglutination observed. *E coli* SHl showed a titer of about 1/16 with both bead types. The recombinant strain HU849 showed a titer of about 1/32 with both bead types. The recombinant strain HU1093 showed a titer of about 1/32 for the globoside coated beads but did not agglutinate digalactoside coated beads at any concentration. *E. coli* strain P678-54 was negative with both beads at all concentrations.

An additional embodiment as a composition of matter is a bacterial RSP that binds specifically to the Anton blood group antigen. Certain *Haemophilus influenzae* strains, for example strain 770235, agglutinate erythrocytes that have the Anton antigen on their surface but do not agglutinate cells lacking the Anton antigen. *H. influenzae* bacteria that express this Anton specific RSP, or purified Anton RSP, were used to test for the presence of the Anton antigen on erythrocytes.

One specific method for a simple and easy blood typing test comprises the growing of bacteria in a fimbriae enhancing environment, collecting the bacteria, gently resuspending the bacteria with a drop of blood and measuring the amount of hemagglutination.

An alternative method comprises growing the bacteria in a fimbriae enhancing environment, collecting the bacteria, removing the fimbriae-like growth from the surface of the bacteria, resuspending the fimbriae with a drop of blood and measuring the amount of hemagglutination.

Further embodiments include preserving and storing the bacteria and/or fimbriae for future use. The stored bacteria and/or fimbriae are resuspended when needed and added to a drop of blood or added to tissue to test the specific areas containing the antigen of interest. The bacteria and/or fimbriae can be used to test erythrocytes and tissue, to detect disease or to monitor the treatment of the disease.

Because of the ability to preserve the fimbriae kits are used to detect blood groups as well as disease. The kits are designed to meet a variety of needs. For example, one embodiment for typing antigens is a kit comprised of at least one RSP having a specificity to antigens selected from the group consisting of En(a+), En(a−), Dr+, Dr−, Dr−$CM^R$, KK, Kk, kk, $K_o$, Pglobo and Anton. The kit can detect the antigen on either erythrocytes or tissues. When more than one RSP is incorporated into the kit a battery of tests is performed to detect multiple antigens.

An additional embodiment is a kit which further comprises at least one control antigen sample selected from the group consisting of En(a+), En(a−), Dr+, Dr−, Dr−$CM^R$, KK, Kk, kk, $K_o$, Pglobo and Anton. The control antigen enables users to easily determine the specificity and reactivity of the RSP under each laboratory's conditions for the specific blood group.

Method for Purification of RSPs

The RSPs were purified by a method comprised of the steps of growing bacteria in a fimbriae enhancing environment, removing the fimbriae from the bacteria and preserving the fimbriae. One specific method of purification employed modifications of the method of Korhonen et al., Infection and Immunity 27: 569-579 (1980), the disclosure of which is incorporated by reference.

The fimbriae were purified from *E. coli* grown for approximately 48 hours in static Luria growth (fimbriae enhancing environment). The *E. coli* formed pellices on the culture surfaces and the cells were heavily fimbriated. These cells were harvested by centrifugation (4° C., 400×g) and suspended in a cold Tris buffer (10 mM Tris-HCl, pH 7.5, containing 0.5% $NaN_3$). The fimbriae were detached from the bacterial cells by homogenization. After further centrifugation the fimbriae were found in the supernatant. This procedure did not cause cell breakage, but did result in the removal of the fimbriae from the surface. Further purification was done at about 4° C.

Ammonium sulphate was added to the supernatant to obtain approximately a 20 to 50% saturation. After standing overnight the precipitate was collected by centrifugation (1 hr, 10,000×g), suspended in Tris buffer and dialyzed for approximately 48 hours. After dialysis sodium deoxycholate (DOC) was added to the suspension to a final concentration of about 0.5% (wt/vol) (DOC buffer) and the suspension dialyzed against the DOC buffer for approximately 48 hours. Although the preferred embodiment employed about 48 hours dialysis, shorter dialysis times may be used. However the longer the time, the easier the final purification. DOC caused disaggregation of fimbriae-fimbriae and fimbriae-lipopolysaccharide aggregates. After further centrifugation (10 min., 10,000×g) the supernatant contained the fimbriae protein and the pellet contained most of the outer membrane proteins. The supernatant was then concentrated in an Amicon ultrafiltration cell at room temperature.

After concentration and dialysis against Tris buffer, urea was added to a final concentration of approximately 6M. After storage at room temperature for about 2 hours, the solution was eluted through a 40×1.6 cm Sepharose CL-4B column with urea buffer. Almost all of the fimbriae proteins did not penetrate the gel and were eluted in the void volume of the column. The elution volume of the fimbriae subunits was estimated to be about 20 ml. Increasing the time of incubation with the 6M urea did not change the elution profile. This demonstrated the stability of the fimbriae once they have been removed from the bacterial surface and confirmed that the fimbriae maintain their native conformation and size. The fimbriae were further purified by dialysis with distilled water. These fimbriae can be used fresh or preserved for long term storage. The preserved fimbriae are included in kits for blood testing. In the preferred embodiment the kits contain control antigen samples as well as preserved fimbriae.

The specific polymeric fimbriae thus isolated were further characterized. Table 6 shows the amino acid compositions and molecular weight on SDS-PAGE for the receptor specific proteins.

TABLE 6

| MW-SDS-PAGE (Kd) Amino Acid | Amino acid composition of RSP | | | | |
|---|---|---|---|---|---|
| | EN (17.5 Kd) | Pglobo (19.5 Kd) * % of total | Dr (15 Kd) | $P_1$ (19.5 Kd) | DrCM$^R$ (16 Kd) |
| Ile | 5.1 | 3.9 | 3.5 | 3.9 | 3.4 |
| Gly | 8.9 | 13.8 | 15.6 | 14.5 | 16.2 |
| Leu | 5.1 | 5.9 | 6.9 | 5.9 | 6.8 |
| Val | 10.8 | 11.2 | 6.1 | 11.2 | 6.0 |
| Tyr | 1.9 | 1.3 | 0.0 | 1.3 | 0.0 |
| Thr | 10.8 | 8.6 | 13.0 | 8.6 | 12.8 |
| Asn | 6.4 | 6.6 | * | 6.6 | * |

TABLE 6-continued

| MW-SDS-PAGE (Kd) Amino Acid | Amino acid composition of RSP | | | | |
|---|---|---|---|---|---|
| | EN (17.5 Kd) | Pglobo (19.5 Kd) * % of total | Dr (15 Kd) | $P_1$ (19.5 Kd) | DrCM$^R$ (16 Kd) |
| Asp | 5.1 | 7.2 | 12.1 | 7.2 | 12.8 |
| Phe | 4.5 | 5.3 | 1.7 | 5.3 | 1.7 |
| Pro | 1.9 | 3.3 | 1.7 | 3.3 | 1.7 |
| Lys | 3.8 | 7.9 | 3.5 | 7.9 | 3.4 |
| Gln | 6.4 | 4.6 | * | 4.6 | * |
| Glu | 1.9 | 3.9 | 8.6 | 3.9 | 8.5 |
| Ala | 13.4 | 11.8 | 5.2 | 11.2 | 5.1 |
| Ser | 8.3 | 1.3 | 1.5 | 1.3 | 9.4 |
| Met | 0.6 | 0.6 | 2.6 | 0.6 | 2.6 |
| His | 2.5 | 1.3 | 2.6 | 1.3 | 2.6 |
| Lys | 1.3 | 1.3 | 2.2 | 1.3 | 2.1 |
| Arg | 1.3 | 0.0 | 5.2 | 0.0 | 5.1 |
| Trp | 0.0 | 0.0 | 0.0 | 0.0 | 0.0 |

*asn/asp or glu/gln were not separated and is given as one value.

Some of the receptor specific proteins were further characterized by determining the N-terminal amino acid sequences.

TABLE 7

| N—terminal amino acid sequence for receptor specific sequences | | | | | | | | | | | | | |
|---|---|---|---|---|---|---|---|---|---|---|---|---|---|
| DrCM$^R$: | Asn | Phe | Thr | Ser | Ser | Gly | Thr | Asn | Gly | Lys | Val | Asp | Leu |
| | Thr | Ile | Thr | Glu | Glu | Lys | Arg | Val | Thr | Val | Glu | | |
| P: | Ala | Pro | Thr | Ile | Pro | Gln | Gly | Gln | Gly | Lys | Val | Thr | Phe |
| | Asn | Gly | Thr | Val | Val | Asp | Ala | Pro | Cys | Ser | Ile | | |
| Pglobo: | Ala | Pro | Thr | Ile | Pro | Gln | Gly | Gln | Gly | Lys | Val | Thr | Phe |
| | Asn | Gly | Thr | Val | Val | Asp | Ala | Pro | Cys | Ser | Ile | | |
| En(a): | Ala | Thr | Thr | Val | Asn | Gly | Gly | Thr | Val | His | Phe | Lys | Gly |
| | Glu | Val | Val | Asn | Ala | Ala | Cys | Ala | Val | Asn | Met | | |

Fixation Procedure for Receptor Specific Proteins

The method of preserving fimbriae included the step of adding a preserving agent selected from the group consisting of metabolic poisons, chelaters, radiation, heat and paraformaldehyde, formaldehyde and gluteraldehyde. Metabolic poisons include azide, arsenic, thimerosal and cyanide. Chelaters include EDTA, EGTA and citrate. Radiation include X, UV and γ. In general the procedure included growing strains of bacteria to confluence on appropriate fimbriae enhancing media. About 24 hours later the bacterial cells were collected and mixed in a buffer to form a homogeneous suspension. At this point a preserving agent was added to the suspension and the suspension was stored for a short period of time at room temperature. After a short period at room temperature the bacterial cells could be removed from the suspension, washed, resuspended and stored in a cool place.

For example, E. coli strains IH11128 and BN406, which contain RSP specific to Dr, were grown overnight on brain-heart infusion or L agar plates. After collection the bacterial cells were suspended in phosphate buffered saline (pH 7.2) and mixed gently to obtain a homogeneous suspension and a preserving agent was added. In one specific embodiment approximately 1.8% paraformaldehyde was used as the preserving agent. Approximately 0.5% formaldehyde may also be used as a preserving agent. Although the length of time of storage at room temperature was not critical, in the preferred embodiment it ranges from 3 minutes to 10 minutes, with 5 minutes yielding satisfactory results. The cells were then washed and stored in buffer. The preferred buffer is a phosphate buffered saline containing about 0.05% sodium azide and about 2% D-mannose. This suspension was stored at about 4° C. This suspension can be used for agglutination tests for up to at least 1 year.

Method of Hemagglutination Testing

The hemagglutination test can be performed with fresh or stored reagent. Approximately one drop of the reagent was added to about one drop of erythrocytes. Hemagglutination, if it occurs, was almost immediate and the results were read in about two to five minutes. The hemagglutination titer is determined by serially diluting the reagent. In one preferred embodiment positive and/or negative controls were tested at the same time as the unknown blood. The test was usually performed at about 1:64 to 1:128 dilutions. Since a negative reaction will show no visible hemagglutination at any dilution, the use of controls essentially eliminates false tests.

Method of Tissue Testing and Staining

The testing of tissue for the presence and organization of specific antigens can be done with fresh or stored reagents and with whole bacteria or purified RSP. Several dilutions of RSP can be used to quantify the amount of antigen expressed in tissue substructures. One procedure included conjugating bacteria or RSP with a fluorescent indicating system or an enzymatic method; sectioning frozen tissue into thin slices; fixing the frozen tissue sections on glass slides with about 3.5% paraformaldehyde; adding approximately 2 drops of reagents; incubating for about 30 minutes in a humidified chamber at room temperature; washing unbound reagent from the slide; viewing the slide with a fluorescence microscope; and determining the binding of bacteria or RSP by visualization.

Another embodiment of the procedure included sectioning frozen tissue into thin slices, fixing the frozen tissue slices on glass slides, adding bacteria or RSPs dropwise; incubating for about 30 minutes and washing unbound reagent from the slide; detecting the bound reagent by an indirect immunofluorescence method or enzyme linked system. In one embodiment the indirect immunofluorescence assay included conjugating a fluorescent dye to polyclonal or monoclonal antibody specific for the RSP; adding about two drops of this reagent to the RSP treated slides; incubating for about 30 minutes; washing to remove unbound antibody; and determining the binding by visualization of the antibody-RSP complexes in a fluoresence microscope. Alternatively, the indirect immunofluorescence can include adding unlabeled primary antibody specific for the RSP to the frozen tissue slices fixed on slides; incubating for about 30 minutes; washing to remove unbound material; adding a labeled second antibody specific for the primary antibody; incubating for about 30 minutes; washing to remove unbound antibody; and determining binding by visualization in a microscope.

Specific Example of Purification of an En(a) RSP

E. coli strain HU1005 was grown overnight at about 37° C. with aeration in Brain-Heart Infusion Broth containing about 1% glucose (fimbriae-enhancing broth). After centrifugation the bacteria were collected in the pellet. The bacterial pellet was suspended in about 20 ml of approximately 50 mM sodium phosphate (pH 7.2) with about 2M urea and incubated at approximately 50° C. for about 60 minutes. The suspension was then forced through a needle (about 25 g size) approximately 5 times to remove the fimbriae from the surface. Alternatively, for larger volumes, the fimbriae can be removed from the bacteria by homogenization or blending at about 4° C. The suspension was centrifuged (10 min., 27,000×g) to remove the bacteria. The supernatant was dialyzed to equilibrium against about 50 mM Tris pH 7.0 buffer containing about 0.5M NaCl. After dialysis the suspension was centrifuged (20 min., 17,000×g), the pellet discarded, and the supernatant was again dialyzed to equilibrium against about 50 mM Tris pH 7.0 buffer containing about 5M NaCl. After dialysis the suspension was centrifuged (20 min., 27,000×g), the supernatant discarded and the pellet was resuspended in about 50 mM Tris pH 7.0 buffer. The suspension was then dialyzed to equilibrium against about 10 mM Tris pH 7.5 buffer containing approximately 0.05% sodium azide and about 0.5% DOC. After dialysis the suspension was centrifuged (10 min., 12,000×g), the pellet discarded, and the supernatant dialyzed to equilibrium against about 10 mM Tris pH 7.0 buffer containing about 0.05% sodium azide. After dialysis and centrifugation (10 min., 27,000×g) the supernatant was dialyzed to equilibrium against 50 mM Tris pH 7.0 buffer containing about 5M NaCl. After dialysis and centrifugation (10 min., 27,000×g) the pellet was suspended in approximately 50 mM Tris pH 7.0 buffer containing about 0.85% NaCl. This suspension was dialyzed to equilibrium against about 50 mM sodium phosphate pH 7.2 buffer containing about 6M urea. The suspension was then centrifuged (10 min., 17,000×g) and the supernatant was applied to a Sepharose CL-4B column equilibrated with about 50 mM sodium phosphate pH 7.2 buffer containing about 6M urea. The En(a) RSP was excluded from this column and was contained in the void volume. Approximately one-half milliliter fractions were collected from the column and dialyzed to equilibrium against about 50 mM Tris pH 7.0 buffer containing about 5M NaCl. After centrifugation (10 min., 15,000×g) the pellet was resuspended in 50 mM Tris pH 7.0 buffer containing 0.85% saline and either used fresh or preserved and stored for later use.

Molecular Cloning of Fimbriae

All of the fimbriae can be purified and isolated from artificially growing, naturally occurring E. coli in the laboratory. However, this procedure is tiresome, difficult and in some cases may lead to fimbriae which are not suitable for detecting erythrocyte and/or tissue antigens. This problem was alleviated by the present invention. One embodiment includes, as a composition of matter, a recombinant DNA E. coli having a gene coding for a RSP, wherein the RSP has a specificity for antigens selected from the group consisting of En(a+), En(a−), Dr+, Dr−, Dr−$CM^R$, KK, Kk, kk, $K_o$, P, Pglobo, M and Anton. The advantage of incorporating the RSP into a recombinant molecule is that specific fimbriae can be grown and collected. Because large amounts of fimbriae specific to certain blood groups are grown, kits to detect a variety of specific blood groups are easily and economically made. Thus, it is feasible to blood type for rare blood groups and to detect and monitor disease.

A specific embodiment, as a composition of matter, is a recombinant DNA E. coli having a plasmid expressing the RSP with a specificity for antigens selected from the group consisting of Dr+ and Dr−. Bacteriophage λ transducing particles carrying recombinant cosmid molecules with a portion of the IH11128 genome were prepared and used to transduce *E. coli* HB101. From the resultant ampicillin-resistant transducents a colony specific to Dr+ was isolated, for example BN400. The plasmid DNA was isolated from BN400 and used to transform *E. coli* EC901. The newly obtained transformant, was identified as BN401. The isolated plasmids are digested with restriction endonuclease Hind III into five fragments. A 12 Kb Hind III fragment was subcloned into a plasmid vector pACYC184 to form pBJN406. *E. coli* strains EC901 and P678-54 were transformed with pBJN406. The resulting strains BN406 and BN407, respectively, exhibited strong agglutination with Dr+ erythrocytes.

The hemagglutination ability of natural strain *E. coli* IH11128 and recombinant DNA strains BN406 and EC901 were measured by observing the resultant hemagglutination, if any, when dilutions of bacteria were mixed with erythrocytes. The naturally occurring strain IH11128 showed a titer of 1/32 while the recombinant strain BN406 had a titer of 1/256. EC901 was negative at all concentrations indicating that this recombinant strain did not contain fimbriae reactive to the Dr+ antigen.

The attachment capacities of BN406, IH11128 and EC901 were also tested by measuring the ability of the bacteria to adhere to frozen sections of human kidneys. FITC-labeled IH11128 and BN406 adhered to frozen human kidneys in a localized binding pattern. BN406 bound to interstitial elements and to Bowman's capsule. The attachment and binding pattern of the recombinant clone was stronger and more specific than that of the natural strain. Furthermore the natural strain exhibited additional attachment to glomerular elements. The EC901 strain showed only non-specific adhesion to the cells. The binding specificity was further characterized by indirect immunofluorescence analysis. The advantage of the indirect immunofluorescence method is that only those cells binding bacteria that express 075X fimbriae are stained. The recombinant DNA strain BN406 bound selectively to the interstitial area and Bowman's capsule of the human kidney. The binding of the BN406 strain resulted from the specific binding capacity of the cloned recombinant DNA.

A further example of an *E. coli* strain which recognized specific elements in the renal interstitium is BN53. The cloned fimbriae elements from IH11128 provide a tool to observe the role of 075X adhesion in urinary tract infection at the molecular level.

Characterization of the 075X Fimbriae

The surface structures (fimbriae), were purified from the BN406 and IH11128 strains and analyzed on SDS-PAGE. The isolated surface structures revealed a peptide band with the apparent molecular weight of about 15,000 for both IH11128 and BN406 strains. Furthermore, another intensely stained band with the apparent molecular weight of about 27,000 was observed in the BN406 but not in the IH11128 bacterial cells. Electron microscopic studies of the bacterial cells of IH11128, recombinant BN406 and recombinant EC901 showed that the fimbriae-like structures were seen on negatively stained intact cells of BN406 and IH11128 but not on EC901. The electron micrographs confirmed that the recombinant DNA BN406 strain was producing RSP on its surface and the binding studies established that the RSP was detecting the human Dr antigen on the surface of kidney cells and erythrocytes. The purified fimbriae bound specifically to the basement membrane of the kidney tubules and to Bowman's capsule. Additionally, Bowman's capsule showed a two-layer substructure, intensely stained with the fimbriae. The purified fimbriae were active in hemagglutination and in specific binding to kidney substructures. Thus the cloned hemagglutination was associated with the extracellular proteinaceous structures of fimbrial morphology. This invention describes a strain of *E. coli* which incorporates the genes coding for fimbriae which bind the Dr+ antigen. Because this recombinant DNA strain and the protein specific RSP was generated in sufficient quantities for low cost blood typing, it is now economically feasible to test for rare phenotypes.

The cloned RSPs can be used to test the presence of blood group antigens on the erythrocytes for blood typing, as well as, to study tissues for the presence of surface antigens on tissues. The tissue sensitivity showed differential detection of disease organisms and specific tissue areas. The RSP method provides a new way to detect specific diseases, as well as, to detect specific areas of the tissues infected.

The differential binding between the IH11128 and BN406 established that there is more than one binding factor present in the parent strain, IH11128. The ability to clone the genetic structure for production of RSPs also included the ability to subclone fragments of the RSP genetic structure to develop specific probes for binding to the tissue antigens.

The purified fimbriae from the recombinant clones were characterized by their ability to recognize substructures from the kidney including tubular basement membrane and Bowman's capsules. Antigen expressed in the kidney substructure served as a receptor for the uropathogenic *E. coli*. The Dr blood group antigen is a component of the IFC blood group complex and is a receptor for fimbriae of uropathogenic *E. coli*.

The invention includes a procedure for identifying the receptor structure on erythrocytes for the Dr hemagglutinin and involves a method of systematically studying erythrocytes representing the different blood group systems. This systematic search provided a model for the identification of new hemagglutinin RSPs. This model approach identified erythrocyte blood group systems, including public antigens, i.e. common phenotypes, as well as silent (minus-minus) antigens, i.e. rare phenotypes, that express no antigen of a given system. This systematic analysis is an excellent tool for the study of unknown receptors for hemagglutinins of *E. coli* and other species.

Although the M blood group antigen recognized by *E. coli* IH11165 is an amino acid, Dr RSP showed no or little specific amino acid inhibition of binding. However, modified tyrosine or oligopeptide containing tyrosine may be part of the receptor moiety for the Dr hemagglutinin. The strong inhibitory activity of chloramphenicol suggested that the receptor structure must be very similar to this compound.

The differential binding of the Dr+ RSP to the basement membrane and Bowman's capsule provided methods for detecting diseases of these tissues and for monitoring the efficacy of the treatment. Damage to these kidney structures is characteristic of a disease called interstitial nephritis. The DR RSP can be used as a histological stain to visualize these structures in tissue biopsies and to determine their integrity.

Furthermore, Dr− individuals are prone to certain bowel syndromes including Crohn's disease. Since histological staining with the Dr RSP showed a very high density of the Dr antigen in the bowel tissue of Dr+ individuals, the presence and organization of the DR antigen in bowel tissues of both Dr− and Dr+ individuals who have Dr associated bowel disease can be characterized.

Dr+ is a high frequency blood group antigen and is part of the IFC blood group system. Its biological properties, frequency of silent phenotypes in the population, tissue distribution and molecular structure are not completely known. The present invention provides the tools to elucidate these unknown biological properties. Because the Dr+ hemagglutinin recognized the Dr antigen, this provides a method of detecting in the population Dr− and IFC− individuals. Identification of Dr− individuals provides an opportunity to examine the relationship between the IFC silent phenotype and digestive tract and other diseases. The high specificity of the Dr hemagglutinin offers an interesting tool for the isolation and identification of Dr antigen or tissue substructures containing it, especially since the composition of basement membrane is not well known.

Fimbriae used and described in this invention have a variety of purposes in the clinical environment. These RSPs can be used for typing blood and tissue. The ability to extensively type blood correctly is necessary in a variety of situations, including blood transfusion, tissue transplantation and paternity testing. Furthermore the fimbriae can be used to examine tissue and thus provide a way for analyzing the diseases that attack certain tissues. The method and RSPs described provide an ideal method of examining the pathogenesis of diseases associated with binding to surface antigens.

One skilled in the art will readily appreciate that the present invention is well adapted to carry out the objects and attain the ends and advantageous mentioned, as well as, those inherent therein. The composition of matter and methods described herein are presently representative of the preferred embodiments, are intended to be exemplary and are not intended as limitations on the scope. Changes therein and other uses will occur to those skilled in the art which are encompassed within the spirit of the invention or defined by the scope of the appended claims.

What is claimed is:

1. As a composition of matter, a receptor specific protein selected from the group consisting of En, Dr, DrCM$^R$ and Pglobo, said receptor specific protein,
   being isolated from bacteria,
   having a polymerized fimbriae structure,
   having the following antigenic specificity to erythrocyte antigens;

| Receptor Specific Protein | Erythrocyte Antigen |
|---|---|
| En | En(a+), En(a−) |
| Dr | Dr+, Dr− |
| DrCM$^R$ | DrCM$^R$ |
| Pglobo | Pglobo | having the following amino acid composition:

| Amino Acid | En | Pglobo | Dr | DrCM$^R$ |
|---|---|---|---|---|
| | | % of total | | |
| Ile | 5.1 | 3.9 | 3.5 | 3.4 |
| Gly | 8.9 | 13.8 | 15.6 | 16.2 |
| Leu | 5.1 | 5.9 | 6.9 | 6.8 |
| Val | 10.8 | 11.2 | 6.1 | 6.0 |
| Tyr | 1.9 | 1.3 | 0.0 | 0.0 |
| Thr | 10.8 | 8.6 | 13. | 12.8 |
| Asn | 6.4 | 6.6 | * | * |
| Asp | 5.1 | 7.2 | 12.1 | 12.8 |
| Phe | 4.5 | 5.3 | 1.7 | 1.7 |
| Pro | 1.9 | 3.3 | 1.7 | 1.7 |
| Lys | 3.8 | 7.9 | 3.5 | 3.4 |
| Gln | 6.4 | 4.6 | * | * |
| Glu | 1.9 | 3.9 | 8.6 | 8.5 |
| Ala | 13.4 | 11.8 | 5.2 | 5.1 |
| Ser | 8.3 | 1.3 | 1.5 | 9.4 |
| Met | 0.6 | 0.6 | 2.6 | 2.6 |
| His | 2.5 | 1.3 | 2.6 | 2.6 |
| Lys | 1.3 | 1.3 | 2.2 | 2.1 |
| Arg | 1.3 | 0.0 | 5.2 | 5.1 |
| Trp | 0.0 | 0.0 | 0.0 | 0.0 | having the following molecular weight on SDS-PAGE electrophoresis: En=17,500, Dr=15,000, Dr−CM$^R$=16,000, and Pglobo=19,500; and
having the following N-terminal amino acid sequences:

| | |
|---|---|
| En | Ala Thr Thr Val Asn Gly Gly Thr Val His Phe Lys Gly Glu Val Val Asn Ala Ala Cys Ala Val Asn Met |
| DrCM$^R$ | Asn Phe Thr Ser Ser Gly Thr Asn Gly Lys Val Asp Leu Thr Ile Thr Glu Glu Lys Arg Val Thr Val Glu |
| Pglobo | Ala Pro Thr Ile Pro Gln Gly Gln Gly Lys Val Thr Phe Asn Gly Thr Val Val Asp Ala Pro Cys Ser Ile |
| Dr | Thr Phe Gln Ser Gly Thr Thr Gly Ile Thr Thr Leu Thr Val |

2. The receptor specific protein of claim 1, wherein said receptor specific protein is isolated from the group of bacteria consisting of *Escherichia coli* strain HU1005 for En, *Escherichia coli* strain IH11128 for Dr, *Escherichia coli* strain SH175 for Dr−CM$^R$ and *Escherichia coli* strain HU784 for Pglobo.

3. As a composition of matter, a receptor specific protein selected from the group consisting of En, Dr, DrCM$^R$ and Pglobo, said receptor specific protein,
   being isolated from bacteria,
   having a polymerized fimbriae structure,
   having the following antigens specified to tissue surface antigen:

| Receptor Specific Protein | Tissue Surface Antigen |
|---|---|
| En | En(a+), En(a−) |
| Dr | Dr+, Dr− |
| DrCM$^R$ | DrCM$^R$ |
| Pglobo | Pglobo | having the following amino acid composition:

| Amino Acid | En | Pglobo | Dr | DrCM$^R$ |
|---|---|---|---|---|
| | | % of total | | |
| Ile | 5.1 | 3.9 | 3.5 | 3.4 |
| Gly | 8.9 | 13.8 | 15.6 | 16.2 |
| Leu | 5.1 | 5.9 | 6.9 | 6.8 |
| Val | 10.8 | 11.2 | 6.1 | 6.0 |
| Tyr | 1.9 | 1.3 | 0.0 | 0.0 |
| Thr | 10.8 | 8.6 | 13. | 12.8 |
| Asn | 6.4 | 6.6 | * | * |
| Asp | 5.1 | 7.2 | 12.1 | 12.8 |
| Phe | 4.5 | 5.3 | 1.7 | 1.7 |

-continued

| Amino Acid | En | Pglobo | Dr | DrCM$^R$ |
| --- | --- | --- | --- | --- |
| | | % of total | | |
| Pro | 1.9 | 3.3 | 1.7 | 1.7 |
| Lys | 3.8 | 7.9 | 3.5 | 3.4 |
| Gln | 6.4 | 4.6 | * | * |
| Glu | 1.9 | 3.9 | 8.6 | 8.5 |
| Ala | 13.4 | 11.8 | 5.2 | 5.1 |
| Ser | 8.3 | 1.3 | 1.5 | 9.4 |
| Met | 0.6 | 0.6 | 2.6 | 2.6 |
| His | 2.5 | 1.3 | 2.6 | 2.6 |
| Lys | 1.3 | 1.3 | 2.2 | 2.1 |
| Arg | 1.3 | 0.0 | 5.2 | 5.1 |
| Trp | 0.0 | 0.0 | 0.0 | 0.0 | having the following molecular weight on SDS-PAGE electrophoresis: En=17,500, Dr=15,000, Dr−CM$^R$=16,000, and Pglobo=19,500; and having the following N-terminal amino acid sequences:

| | |
| --- | --- |
| En | Ala Thr Thr Val Asn Gly Gly Thr Val His Phe Lys Gly Glu Val Val Asn Ala Ala Cys Ala Val Asn Met |
| DrCM$^R$ | Asn Phe Thr Ser Ser Gly Thr Asn Gly Lys Val Asp Leu Thr Ile Thr Glu Glu Lys Arg Val Thr Val Glu |
| Pglobo | Ala Pro Thr Ile Pro Gln Gly Gln Gly Lys Val Thr Phe Asn Gly Thr Val Val Asp Ala Pro Cys Ser Ile |
| Dr | Thr Phe Gln Ser Gly Thr Thr Gly Ile Thr Thr Leu Thr Val |

4. The receptor specific protein of claim 3, wherein said receptor specific protein is isolated from the group of bacteria consisting of *Escherichia coli* strain HU1005 for En, *Escherichia coli* strain IH11128 for Dr, *Escherichia coli* strain SH175 for Dr−CM$^R$ and *Escherichia coli* strain HU784 for Pglobo.

* * * * *

UNITED STATES PATENT OFFICE
CERTIFICATE OF CORRECTION

Patent No. 4,882,425  Dated November 21, 1989

Inventor(s) Richard A. Hull; Sheila I. Hull, Bogdan Nowicki

It is certified that error appears in the above-identified patent and that said Letters Patent is hereby corrected as shown below:

Column 4, Line 28, Table 1, under column headed Hemagglutination, fifth row, add -- + --.

Column 4, Line 35, Table 1, under column headed Hemagglutination, 12th row, add -- + --.

Column 4, Line 37, Table 1, under column headed Hemagglutination, 14th row, add -- + --.

Column 12, Line 32, in Table 7, add the following:

--Dr:  Thr Phe Gln Ser Gly Thr Thr Gly Ile
       Thr Thr Leu Thr Val --

Column 16, Line 7, change "hemagglutination" to -- hemagglutinin --.

Signed and Sealed this

Fifteenth Day of January, 1991

Attest:

HARRY F. MANBECK, JR.

Attesting Officer            Commissioner of Patents and Trademarks